(12) United States Patent
Rahimian et al.

(10) Patent No.: US 8,758,263 B1
(45) Date of Patent: Jun. 24, 2014

(54) SYSTEMS AND METHODS FOR FRAMELESS IMAGE-GUIDED BIOPSY AND THERAPEUTIC INTERVENTION

(75) Inventors: Javad Rahimian, Irvine, CA (US); Amir Rombod Rahimian, Irvine, CA (US)

(73) Assignee: Voxel Rad, Ltd., Irvine, CA (US)

( * ) Notice: Subject to any disclaimer, the term of this patent is extended or adjusted under 35 U.S.C. 154(b) by 580 days.

(21) Appl. No.: 12/915,847

(22) Filed: Oct. 29, 2010

Related U.S. Application Data

(60) Provisional application No. 61/280,176, filed on Oct. 31, 2009.

(51) Int. Cl.
*A61B 10/00* (2006.01)
*A61B 19/00* (2006.01)

(52) U.S. Cl.
USPC ............ 600/562; 600/415; 600/417; 606/130

(58) Field of Classification Search
None
See application file for complete search history.

(56) References Cited

U.S. PATENT DOCUMENTS

| | | |
|---|---|---|
| 4,132,896 A | 1/1979 | Klotz et al. |
| 4,237,901 A | 12/1980 | Taenzer |
| 4,249,106 A | 2/1981 | Maruyama et al. |
| 4,583,538 A | 4/1986 | Onik et al. |
| 5,067,981 A | 11/1991 | Hooykaas |
| 5,207,223 A | 5/1993 | Adler |
| 5,222,499 A | 6/1993 | Allen et al. |
| 5,278,886 A | 1/1994 | Kobiki et al. |
| 5,394,875 A | 3/1995 | Lewis et al. |
| 5,397,329 A | 3/1995 | Allen |
| 5,411,026 A | 5/1995 | Carol |
| 5,427,097 A | 6/1995 | Depp |
| 5,446,548 A | 8/1995 | Gerig et al. |
| 5,447,154 A | 9/1995 | Cinquin |

(Continued)

FOREIGN PATENT DOCUMENTS

| | | |
|---|---|---|
| EP | 1004272 A | 5/2000 |
| JP | 62-206798 | 9/1987 |

(Continued)

OTHER PUBLICATIONS

ACR Standard for the performance of Stereotactic radiosurgery. ACR practice Guideline, 2002; 559-563.

(Continued)

*Primary Examiner* — Corrine M McDermott
*Assistant Examiner* — Todd J Scherbel
(74) *Attorney, Agent, or Firm* — Knobbe Martens Olson & Bear, LLP

(57) ABSTRACT

A system and a method of performing a frameless image-guided biopsy uses imaging, a six-dimensional robotic couch system, a laser guidance system, an optical distance indicator, and a needle control apparatus. A planning CT scan is made of the patient with stereotactic fiduciary markers to localize and produce digitally reconstructed radiographs. Two stereoscopic images are generated using an imaging device to visualize and identify a target tumor. The images are fused with the digitally reconstructed radiographs of the planning CT scan to process tumor location. The tumor location data are communicated to the movable robotic couch to position the target tumor of the patient at a known isocenter location. A biopsy needle is guided with a laser alignment mechanism towards the isocenter at the determined depth using a needle positioning apparatus and an Optical Distance Indicator, and a biopsy sample of the target tumor is obtained.

20 Claims, 11 Drawing Sheets

(56) References Cited

U.S. PATENT DOCUMENTS

| | | | |
|---|---|---|---|
| 5,537,452 | A | 7/1996 | Shepherd et al. |
| 5,588,430 | A | 12/1996 | Bova et al. |
| 5,622,187 | A | 4/1997 | Carol |
| 5,628,315 | A | 5/1997 | Vilsmeier et al. |
| 5,727,554 | A | 3/1998 | Kalend et al. |
| 5,748,700 | A | 5/1998 | Shepherd et al. |
| 5,769,861 | A | 6/1998 | Vilsmeier |
| 5,784,431 | A | 7/1998 | Kalend et al. |
| 5,797,849 | A | 8/1998 | Vesely et al. |
| 5,943,719 | A | 8/1999 | Feldman et al. |
| 5,967,981 | A | 10/1999 | Watrous |
| 5,971,997 | A | 10/1999 | Guthrie et al. |
| 6,006,126 | A | 12/1999 | Cosman |
| 6,019,724 | A * | 2/2000 | Gronningsaeter et al. .... 600/439 |
| 6,031,888 | A | 2/2000 | Ivan et al. |
| 6,035,228 | A * | 3/2000 | Yanof et al. ................... 600/429 |
| 6,052,611 | A * | 4/2000 | Yanof et al. ................... 600/429 |
| 6,076,005 | A | 6/2000 | Sontag et al. |
| 6,120,453 | A | 9/2000 | Sharp |
| 6,144,875 | A | 11/2000 | Schweikard et al. |
| 6,149,592 | A | 11/2000 | Yanof et al. |
| 6,246,898 | B1 | 6/2001 | Vesely et al. |
| 6,256,372 | B1 | 7/2001 | Aufrichtig et al. |
| 6,275,721 | B1 | 8/2001 | Darrow et al. |
| 6,285,902 | B1 | 9/2001 | Kienzle, III et al. |
| 6,301,495 | B1 | 10/2001 | Gueziec et al. |
| 6,307,914 | B1 | 10/2001 | Kunieda et al. |
| 6,314,312 | B1 * | 11/2001 | Wessels et al. ............... 600/427 |
| 6,380,958 | B1 | 4/2002 | Guendel et al. |
| 6,405,072 | B1 | 6/2002 | Cosman |
| 6,464,648 | B1 * | 10/2002 | Nakamura ................... 600/567 |
| 6,470,207 | B1 | 10/2002 | Simon et al. |
| 6,473,634 | B1 | 10/2002 | Barni |
| 6,501,981 | B1 | 12/2002 | Schweikard et al. |
| 6,681,129 | B2 | 1/2004 | Matsuzaki et al. |
| 6,778,850 | B1 | 8/2004 | Adler |
| 7,318,805 | B2 | 1/2008 | Schweikard et al. |
| 8,295,435 | B2 * | 10/2012 | Wang et al. ...................... 378/65 |
| 8,346,344 | B2 * | 1/2013 | Pfister et al. .................. 600/424 |
| 2002/0032453 | A1 | 3/2002 | Cosman |
| 2002/0065461 | A1 | 5/2002 | Cosman |
| 2002/0154728 | A1 | 10/2002 | Morita et al. |
| 2005/0004580 | A1 * | 1/2005 | Jokiniemi et al. ............ 606/130 |
| 2007/0185396 | A1 * | 8/2007 | Zan ................................ 600/415 |
| 2009/0069672 | A1 * | 3/2009 | Pfister et al. .................. 600/424 |
| 2009/0129545 | A1 | 5/2009 | Adler et al. |
| 2009/0198093 | A1 * | 8/2009 | Meissner et al. ................... 600/2 |
| 2010/0063514 | A1 * | 3/2010 | Maschke ....................... 606/130 |
| 2012/0215094 | A1 * | 8/2012 | Rahimian et al. ............. 600/414 |

FOREIGN PATENT DOCUMENTS

| | | |
|---|---|---|
| JP | 5-188199 | 7/1993 |
| JP | 6-502330 | 3/1994 |
| JP | 6-181918 | 7/1994 |
| JP | 8112272 | 5/1996 |
| JP | A-10-201863 | 8/1998 |
| JP | 11-019082 | 1/1999 |
| JP | 2000-201922 | 7/2000 |
| JP | 2000-217810 | 8/2000 |
| JP | 2008023347 | 2/2008 |
| JP | 4718551 | 7/2011 |
| WO | WO 92/06644 | 4/1992 |
| WO | WO 97/40766 | 11/1997 |
| WO | WO 00/07669 | 2/2000 |

OTHER PUBLICATIONS

Brommeland T, Hennig R. Mechanical accuracy of a new stereotactic guide. Acta Neurochir (Wien). 2000; 142(4): 449-54.

Chen, J.C.T., Bugoci D.M., Girvigian M.R., Miller M.J., Arellano A, Rahimian J. Control of brain metastases using frameless image-guided radiosurgery. Neurosurgical Focus, Dec. 2009; 27(6): 1-7.

Chen J.C.T., Rahimian J., Girvigian, M.R., Miller, M.J. Contemporary methods of radiosurgery treatment with the Novalis linear accelerator system. Neurosurgical Focus, Dec. 2007; 23(6): 1-10.

Chen, J.C.T., Girvigian, M., Greathouse, H., Miller, M., Rahimian, J. Treatment of trigeminal neuralgia with linear accelerator radiosurgery: initial results. Journal of Neurosurgery, vol. 101, Supplement 3 101:346-26, 2004.

Coste-Manière, È., "Robotic whole body stereotactic radiosurgery: clinical advantages of the CyberKnife® integrated system", The International Journal of Medical Robotics+Computer Assisted Surgery, 2005, www.roboticpublications.com, pp. 28-39.

Dorward NL, Paleologos TS, Alberti O, Thomas DG. The advantages of frameless stereotactic biopsy over frame-based biopsy. Br J Neurosurg. Apr. 2002; 16(2):110-18.

Drzymala RE, Klein EE, Simpson JR, Rich KM, Wasserman, TH, Purdy JA. Assurance of high quality linac-based stereotactic radiosurgery. International Journal of Radiation Oncology Biology Physics. Sep. 30, 1994; 30(2): 459-472.

Dupuy DE, Rosenberg AE, Punyaratabandhu T, Tan MH, Mankin HJ. Accuracy of CT-guided needle biopsy of musculoskeletal neoplasms. AJR Am J Roentgenol. Sep. 1998; 171(3):759-62.

English Abstract, JP8112272 published May 7, 1996, 1 page.

http://en.wikipedia.org/wiki/Brain_pacemaker, in 2 pages, Jan. 26, 2011.

Examination Report for European Patent Application No. 01 970 945.0, dated Jan. 16, 2007, 7 pages.

Examination Report for European Patent Application No. 01 970 945.0, dated Feb. 23, 2010, 6 pages.

Khan, Faiz M. Physics of Radiation Therapy, 3rd ed. Lippincott Williams & Wilkins, 2003. Chapter 21: 507-520.

Larsson, B., Lidén, K. Sarby, B. Irradiation of Small Structures Through the Intact Skull. Acta Oncologica, 1974, vol. 13, No. 6, pp. 512-534.

Leksell L. The stereotactic method and radiosurgery of the brain. Acta Chirurgica Scandinavica. 1951; 102:316-319.

Leksell L. Cerebral radiosurgery. Acta Chir Scandinavica. 134:585-595, 1968.

Lis, E., Bilsky, M.H., Pisinski, L., Boland, P., Healey, J.H., O'Malley, B., and Krol, G. Percutaneous CT-Guided Biopsy of Osseous Lesion of the Spine in Patients with Known or Suspected Malignancy. American Journal of Neuroradiology 25:1583-1588, Oct. 2004.

Lutz WA, Winston KR, Maleki N. A system for stereotactic radiosurgery with a linear accelerator. International Journal of Radiation Oncology Biology Physics 1988; 14(2):373-381.

Mack A., Czempiel H., Kreiner H.J., Durr G., and Wowra B. Quality assurance in stereotactic space. A system test for verifying the accuracy of aim in radiosurgery. Medical Physics. Apr. 2002; 29 (4): 561-568.

Malatesta T., Landoni V.,Canne S.delle, et al. Dosimetric, mechanical, and geometric verification of conformal dynamic arc treatment. Journal of Applied clinical Medical Physics. 2003; 4(3):195-203.

Minohara, S. et al., "Respiratory Gated Irradiation System for Heavy-Ion Radiotherapy", Internatinoal Journal of Radiation: Oncology Biology Physics, Pergamon Press, US, vol. 47, No. 4, Jul. 1, 2000, ISSN: 0360-3016.

Rahimian, J., Chen, J.C.T., Girvigian, M.R., Miller, M.J., Rahimian, R. Frame Based and Frameless Precision of BrainLab Novalis © Stereotactic Radiosurgery System. Submitted for Publication, 2009.

Rahimian J, Chen JCT, Rao,A.A., Girvigian M.R., Miller M.J., Greathouse, H.E. Geometrical accuracy of the Novalis stereotactic radiosurgery system for trigeminal neuralgia., J Neurosurg (Suppl 3) 101:351-355, 2004.

Rahimian, J., Girvigian, M.R., Chen, J.C.T., Rahimian, R., Miller, M.J. Geometric Accuracy of Frameless Based Image Guided Stereotactic Radiosurgery of Trigeminal Neuralgia Using BrainLab's Exactrac 6-D Robotic System. International Journal of Radiation Oncology Biology Physics. 75(3): S676. Astro 2009.

Ramaseshan R, Heydarian M. Comprehensive quality assurance for stereotactic radiosurgery treatments. Physics in Medicine and Biology. 2003; 48:N199-N205.

Ryken, T., Meeks, S., Pennington, E., Hitchon, P., Traynelis, V., Mayr, N., Bova, F., Friedman, W., Buatti, J. Initial clinical experience with frameless stereotactic radiosurgery: analysis of accuracy and

(56) References Cited

OTHER PUBLICATIONS feasibility. International Journal of Radiation Oncology Biology Physics, vol. 51, Issue 4, pp. 1152-1158, Nov. 15, 2001.
Supplementary European Search Report for European Patent Application No. 01 970 945.0, dated Oct. 16, 2006, 5 pages.
Supplementary European Search Report for European Patent Application No. 01 970 945.0, dated Apr. 5, 2006, 5 pages.
Supplementary Partial European Search Report, Application No. EP01970945, mailed Jun. 28, 2006.
Verellen D, Linthout N, et. al. Assessment of the uncertainties in dose delivery of a commercial system for LINAC-based stereotactic radiosurgery. International Journal of Radiation Oncolology Biology Physics, May 1, 1999; vol. 44, No. 2: 421-433.
Vinci, JP, Hogstrom, KR, Neck, DW. Accuracy of cranial coplanar beam therapy using an oblique, stereoscopic x-ray image guidance system. Med. Phys. vol. 35, Issue 8, pp. 3809-3819 (Aug. 2008).
Widmann, G., M.D., Image-guided surgery and medical robotics in the cranial area. Biomedical Imaging and Intervention Journal. Feb. 21, 2007; 3(1): 1-9.
Wood, ML, Henkelman RM. Artifacts, in Magnetic resonance imaging. Stark DD, Bradley WG. Editors. vol. 1, 3rd ed. Mosby, Chapter 10: 215-230, 1999.
Wurm RE, Erbel S, Schwenkert I, Gum F, Agaoglu, D, et. al. Novalis frameless image-guided noninvasive radiosurgery: Initial experience. Neurosurgery, Vo. 62, No. 5, May 2008 Supp, pp. A11-A18.
Yeung D, Palta J, Fontanesi J, Kun L. Systematic analysis of errors in target localization and treatment delivery in Stereotactic radiosurgery (SRS). International Journal of Radiation Oncology Biology Phys. Jan. 15, 1994, vol. 28, No. 2: 493-498.
Magjarevic, R., Nagel, J.H., IFMBE Proceedings, vol. 14/1 to 14/6, World Congress on Medical Physics and Biomedical Engineering 2006, held Aug. 27, 2006-Sep. 1, 2006, Table of Contents, dated 2007, in 145 pages.
Park, D.H., Park, J.Y., Chung, Y.G., Shin, I.Y., and Lee, H.K. Frameless Stereotactic Biopsy for the Brain Tumor. IFMBE Proceedings vol. 14/5, vol. 5 Track 17 3143, 2007 in 3 pages.

\* cited by examiner

SYSTEMS AND METHODS FOR FRAMELESS IMAGE-GUIDED BIOPSY AND THERAPEUTIC INTERVENTION

CROSS-REFERENCE TO RELATED APPLICATIONS

This application claims the priority benefit of U.S. Provisional Application Ser. No. 61/280,176, filed on Oct. 31, 2009, the entirety of which is hereby incorporated by reference herein.

BACKGROUND

1. Field of the Invention

The present application relates to devices and methods for frameless image-guided biopsy and/or therapeutic intervention. In particular, the present application relates to devices and methods for frameless image-guided stereotactic, CT, and/or MRI system biopsy, therapeutic intervention and/or drug delivery for tumors using stereoscopic imaging, laser guidance, and/or infrared-based positioning and tracking of patients, utilizing, for example, a six-dimensional (6D) robotic couch system.

2. Description of the Related Art

Medical treatment of a patient often includes a medical professional obtaining a biopsy sample from the patient to evaluate the condition of the patient and plan an appropriate treatment. For example, a surgeon may need to collect a sample to perform a biopsy of a brain tumor prior to further treatment or surgery. Traditional systems and methods for collection of a biopsy sample can be complicated, cumbersome, and may be overly invasive to the patient.

A rigid frame-based stereotactic biopsy system is considered the industry standard for evaluation of histological specimens from targets within the brain. The frame-based system requires attachment of a frame to the skull of a patient to assist the surgeon in locating and collecting a sample from a specific targeted location within the brain. The patient requires anesthesia during the procedure. The frame is typically attached to the patient by invasively inserting four screws into the skull. This frame-based method provides the neurosurgeon with a generally safe (mortality <1%, morbidity 3-4%) and effective (diagnostic yield >95%) means for biopsy retrieval. The frame-based system has advantages over some other biopsy procedures. For example, the frame-based system has provided advantages for patient outcomes compared with freehand (CT-directed) burr-hole biopsy (mortality >5%, morbidity 15%, diagnostic yield 85%).

However, frame-based head fixation can be painful and the head movement limitation can be intolerable to many patients. Furthermore, there is risk of epidural hematoma, cranial fracture, and cerebrospinal fluid (CSF) leak following the application of head pins, and laceration of the scalp with patient movement especially in young children. From the surgeon's perspective, rigid head fixation can also be problematic since the head pins are bulky and limit intraoperative flexibility as well as free movement of surgical instruments. If the patient's head moves relative to a reference arc, the accuracy of the system is greatly reduced, potentially compromising successful execution of the procedure. Unlike surgery, the risks of image-guided frameless biopsy are infinitely less.

Currently, most extra-cranial biopsies are done using CT-guided biopsy, such as, for example, CT-guided spinal biopsy (CTGSB). Recent studies analyzed the accuracy of a CTGSB of osseous spinal lesions in patients with known or suspected underlying malignancy in reference to major variables such as the radiographic appearance of the biopsied lesion and its location within the spinal column. The results showed an overall diagnostic accuracy of CTGSB to be 89%, with a false-negative rate of 11%. Biopsy of lytic lesions yielded an accurate diagnosis in 93% (220 of 236). Despite technical challenges inherent to biopsy of sclerotic lesions, diagnostic accuracy was 76% (63 of 83) and, significantly, 24% (20 of 83) of the results in sclerotic lesions were falsely negative.

CT Guided biopsy can be challenging at times because the patient has to be moved out of the CT gantry to place the needle, thus lowering the precision and causing the high false-negative rate of 11% to 24% for lytic and sclerotic lesions, respectively, and low diagnostic accuracy of 76%. Furthermore, current systems typically do not utilize image fusion that can help delineate the tumor by using high soft tissue contrast imaging provided by MRI, or high metabolic tumor activities information that can be provided by PET scans. Another disadvantage of the CT-guidance is high ionizing radiation exposure to the patient or the interventional radiologist since the patient has to be scanned before, during, and maybe after the needle placement.

SUMMARY OF SOME EMBODIMENTS

The present application provides for improved biopsy retrieval, drug delivery, and other treatments. According to one embodiment of the present application, a frameless image-guided biopsy system utilizes stereoscopic imaging (CT and/or MRI imaging can be used in some embodiments), a 6-Dimentional (6D) Robotic couch system along with infrared cameras, an optical distance indicator, laser guidance for treatment, and a needle positioning device. The depth of the target at any point is preferably determined using the optical distance indicator (ODI) installed on an isocentric C-arm. The accuracy of needle placement to the target can preferably be achieved to within 1 mm. Some treatments may include a technique for frameless stereotactic radiosurgery, as described herein.

According to one aspect of the application a method of performing a frameless image-guided biopsy uses stereoscopic imaging, a six-dimensional robotic couch system along with infrared cameras, a laser guidance system, an optical distance indicator, and a needle control apparatus. The system is adapted to obtain a biopsy sample from a patient with a high degree of accuracy and minimizing adverse patient effects comprises positioning a patient on a movable robotic couch in preparation for the collection of a biopsy sample. A planning CT scan is made of the patient with stereotactic fiduciary markers to produce digitally reconstructed radiographs. At least two stereoscopic images are generated using an imaging device to visualize and identify a target tumor. The at least two stereoscopic images identifying the target tumor are fused with the digitally reconstructed radiographs of the planning CT scan. Tumor location data is processed with a computer using the fused images. Movement instructions are communicated to the movable robotic couch in response to the tumor location data. The movable robotic couch shifts to position the target tumor of the patient at a known isocenter location. A biopsy needle is safely guided with a laser alignment mechanism towards the isocenter. The depth at which a needle is to be inserted to get to the target tumor is determined using the ODI. The position and movement of the needle are controlled with a needle positioning apparatus. The needle is moved into the patient to the desired target tumor location. A biopsy sample of the target tumor is obtained.

According to one embodiment of the application, a system for frameless image-guided biopsy comprises at least one imaging system adapted for capturing a planning CT scan of the patient with stereotactic fiduciary markers to produce digitally reconstructed radiographs of a patient. At least one imaging system is adapted for capturing a plurality of stereoscopic images of a target tumor within a patient. The reconstructed radiographs are adapted to be fused with the plurality of stereoscopic images to provide tumor location data. A six-dimensional, infrared activated computer-controlled, robotic couch system is configured to support the patient during use and adapted to receive tumor location data and shift position in response to data received to position the tumor of the patient at an isocenter location. A laser guidance system is mounted at least partially above the six-dimensional, computer-controlled, robotic couch system and directing a plurality of lasers toward the isocenter location. An optical distance indicator is configured to optically measure the distance from the laser source to the isocenter. The optical distance indicator is adapted to indicate the depth of the target tumor location within the patient. A needle positioning apparatus comprises a needle support and a needle. The needle support is adapted to align the needle with the laser guidance system at a desired entry location. The needle support is adapted to advance the needle to a location within the patient provided by the optical distance indicator. The needle is adapted to be advanced to the target tumor to obtain a biopsy sample from the patient for analysis.

According to one aspect of the application a method of performing a frameless image-guided biopsy uses CT scan imaging. According to one aspect of the application a method of performing a frameless image-guided biopsy uses MRI scan imaging.

According to one system of the application, an apparatus and methodology for image guided stereotactic biopsy/intervention is provided. A patient is preferably positioned on a movable robotic couch in preparation for the collection of a biopsy sample. The technique preferably includes using at least one of various imaging modalities to visualize a tumor, or another structure. Imaging modalities may include, but are not limited to, one or more of an MRI, PET, SPECT, and Ultrasound imaging devices. In one procedure, a tumor is visualized and identified as a target. The image identifying the tumor is preferably fused with a planning CT scan with stereotactic fiduciary markers. Two stereoscopic images are preferably taken to fuse with digitally reconstructed images (DRRs) of the planning CT scan. The image data including the tumor location data is communicated to the robotic table, which can shift to position the tumor at a specific known location. The shifts in six dimensions (e.g., Longitudinal, Lateral, Anterior-Posterior, Pitch, Roll, and Yaw) are achieved using the robotic couch apparatus. Two verification images are preferably taken, and the procedure is repeated until the 6D shifts are less than 0.5 mm or 0.5 degrees. With the tumor located in a known isocentric position, a biopsy needle is preferably guided with a laser alignment mechanism towards the isocenter. The alignment mechanism is preferably focused at all times, and from all directions, towards the isocenter where the tumor is placed using the robotic couch. An optical or ultrasonic distance indicator (ODI) preferably is used to show the depth at which the needle is to be inserted to get to the target using laser guidance. An apparatus is preferably provided that is adapted to support and control the position and movement of the needle. The apparatus is preferably equipped with an articulating arm. Micro-adjustment knobs can be provided in some embodiments to align the needle with the lasers. The needle is preferably moved into the patient as guided by the laser to the desired depth identified by the ODI system. In some embodiments movement of the needle may be automatically controlled using a computer system and/or robotic controls. The overall geometric precision of ≤1 mm is achievable. Other embodiments achieving greater or lesser precision are also contemplated. For some other embodiments, an alternative to laser guidance by using a 6-axis robotic platform is also described.

According to one embodiment for use in brain treatments, the system provides advantages over the frame-based systems by using an aquaplastic mask system that covers the mandible and the forehead to immobilize the patient. The mask is adapted to immobilize the patient during CT imaging and reproduce the same position during image guided biopsy or intervention. Some masks cover the entire face. In some preferred embodiments, however, a customized mask for each patient is adapted to cover the forehead and the mandible to immobilize the patient and make the entire cranium accessible to the surgeon. The patient's head is typically supported by a solid fiberglass couch extension. In some preferred embodiments, a couch extension is made of hard plastic mesh with holes that can support the patient's head without sagging and can be accessible through the holes for performing a posterior surgical approach. In some other techniques, an alternative is to place the patient in a prone position. The stereoscopic imaging fused with DRRs of the planning CT results in accurate determination of the 6D shift on the robotic couch to place the brain tumor accurately at the isocenter. The laser systems installed on the walls or the C-arm focused on the isocenter accurately guide the needle assembly to the isocenter. The ODI system with sub-millimeter accuracy will determine the depth of the target at the approach entry point determined automatically by the navigation computer or by the surgeon or interventional radiologist.

According to some aspects of the application, the preferred technique is minimally invasive with high precision and can be used in most anatomic sites to biopsy, place shunts, perform cyst aspiration, lung edema aspirations, and deliver cytotoxic drugs, and radioactive seed implants. Further, the technique can be used in radiofrequency ablation of tumors such as hepatomas, and cryogenic treatment of tumors such as the prostate tumors. Image guided biopsy can be done almost anywhere in the body. The organs that can potentially be biopsied include, but are not limited to, the liver, lungs, kidneys, pelvis, pancreas, pleura, lymph nodes, bone, and brain.

According to some aspects, in addition to organ biopsies, the methodology of this application can be used to place the leads of "brain pacemakers" or Deep Brain Stimulation (DBS) system that are used to treat people who suffer from epilepsy, Parkinson's disease, major depression and other neurological disorders. The pacemaker is a medical device that is implanted into the brain to send electrical signals into the tissue. Depending on the area of the brain that is targeted, the treatment is called deep brain stimulation (DBS), which causes cortical stimulation. Brain stimulation may be used both in treatment and prevention. Pacemakers may also be implanted outside the brain, on or near the spinal cord (spinal cord stimulation), and around cranial nerves such as the vagus nerve (vagus nerve stimulation), and on or near peripheral nerves in some embodiments.

Advantages of some embodiments include systems and methods for frameless surgical navigation using laser guidance along with infrared cameras and a 6-D robotic couch system that enhances patient comfort and eliminates the risk of complications from head clamp placement in brain biopsies. In some cases, patients can obtain their pre-operative MRI or PET prior to admission. The lack of head fixation precludes the associated risk of skull injury, intracranial injury, or scalp laceration. In addition, a frameless and effectively painless biopsy technique allows greater surgical flexibility than frame based systems in some embodiments. A larger area of the skull is accessible without interference of pins or frames and intra-operative planning of additional target sites can be undertaken without need for complex calculations. Geometric accuracy of within 1 mm to the target can be achieved in some embodiments, allowing for multiple biopsy samples to be taken and to define the margin and stage of the lesion.

Frameless systems provide many advantages over frame-based systems. The operating theatre occupancy and anesthetic time are significantly shorter for frameless systems. In addition, the complication rate in frameless systems is significantly lower than in frame-based systems. Frameless stereotactic biopsy translates into tangible advantages for safety, time and cost when compared with the current industry standard of frame-based biopsy. Current frameless systems are based on infrared guidance detecting fiduciary markers on the patient's skin and surgical instruments. One such system is the BrainLab VectorVision neuronavigation which is widely used in neurosurgery and is an intraoperative, image-guided, frameless, localization system. The system provides real-time responses regarding the location of the surgical instruments. VectorVision is based on passive reflections of infrared flashes received from the reflective markers placed on the surgical instruments and the patient. One problem with the system is the topographic change caused by surgery, which results in discrepancies between the preoperative image data and the surgical site, making navigation inaccurate. The accuracy may be further diminished if the system is used to biopsy tumors that are mobile relative to the fiduciary markers. The position of the target is always calculated relative to the external fiduciary markers, thus limiting the system's overall target-localization accuracy. Other disadvantages are the necessity of constant visual contact between infrared cameras, instruments, and the potential susceptibility to interference through light reflexes on metallic surfaces in the operating environment. The time lag between imaging and surgery, and the sensitivity to skin shift can lead to unfavorable inaccuracies. Bone-implanted fiducials provide invariant spatial registration points with high accuracy and generally serve as the reference standard in registration. The drawbacks of bone-implanted fiducials are their invasiveness, the need for additional surgery, and the possible major patient discomfort for which they should not be left in place for an extended period. The system's target-localizing accuracy of 4.0+/−1.4 mm is reported for cerebral lesions.

Achieving a high degree of accuracy is desirable for clinical application of image-guided surgery and medical robotics. Some embodiments described herein use image guidance by fusing the DRRs with the stereoscopic images based on bony landmarks in which the target coordinates are calculated based on fixed internal structures, thus making the target-localization accuracy superior (preferably ≤1 mm) to other frameless techniques currently used in the clinic. Further, the time lag between imaging and surgery is advantageously not an issue because the DRRs can be fused with the stereoscopic images to obtain the couch 6D shifts. Accordingly, it is unnecessary to do the imaging and surgery in the same day. Thus, another advantage of some aspects of the application is that procedures yield or allow for a more convenient surgical workflow. Additionally, the systems and methods disclosed by the present application are superior to and can replace CT-guided biopsies with techniques involving much less radiation to the patient and the staff.

In addition to the cranial applications, other organs and parts of the body can easily be biopsied using embodiments of this disclosure. Image-guided percutaneous biopsy is advantageously used in obtaining tissue for diagnosis. Most biopsies can be rapidly performed under local anesthesia with little patient discomfort and improved safety. Spinal anatomy is an example of one area of complex anatomy with many adjacent vital structures where knowledge of the anatomy and precise needling technique can be particularly advantageous. The techniques described in this application may be particularly adapted to and well suited for percutaneous biopsy of spinal lesions. The technique can provide a safe and effective method for the evaluation of spinal lesions and may be useful in planning therapy. A low complications rate can be achievable by applying techniques outlined in the present application.

Still other aspects, features, and attendant advantages of the present application will become apparent to those skilled in the art from a reading of the following detailed description of embodiments constructed in accordance therewith, taken in conjunction with the accompanying drawings. Aspects, features, and attendant advantages of the present application provide improvements over known devices, systems and methods. Some devices, systems and methods related to image-guided and stereotactic systems are described in more detail in the following references, each of which is hereby incorporated by reference herein in its entirety. 1. D. H. Park, J. Y. Park, Y. G. Chung, I. Y. Shin and H. K. Lee, Frameless Stereotactic Biopsy for the Brain Tumor, IFMBE Proceedings Vol. 14/5, Volume 5 Track 17 3143; 2. Dorward N L, Paleologos T S, Alberti O, Thomas D G, The Advantages of Frameless Stereotactic Biopsy Over Frame-based Biopsy, Br J Neurosurg, 2002 April, 16(2):110-8; 3. Dupuy D E, Rosenberg A E, Punyaratabandhu T, Tan M H, Mankin H J, Accuracy of CT-guided Needle Biopsy of Musculoskeletal Neoplasms, A J R Am J Roentgenol, 1998 September, 171(3): 759-62; 4. Javad Rahimian, Michael R. Girvigian, Joseph C. T. Chen, Rombod Rahimian, Michael J. Miller, Geometric Accuracy of Frameless Based Image Guided Stereotactic Radiosurgery of Trigeminal Neuralgia Using BrainLab's ExacTrac 6-D Robotic System, ASTRO 2009; 5. Javad Rahimian, Joseph C. T. Chen, Michael R. Girvigian, Michael J. Miller, Rombod Rahimian, Frame Based and Frameless Precision of BrainLab Novalis Stereotactic Radiosurgery System, Submitted for Publication, 2009; 6. Eric Lis, Mark H. Bilsky, Leszek Pisinski, Patrick Boland, John H. Healey, Bernie O'Malley and George Krol, Percutaneous CT-Guided Biopsy of Osseous Lesion of the Spine in Patients with Known or Suspected Malignancy, American Journal of Neuroradiology 25:1583-1588, October 2004; 7. G. Widmann, Image-guided surgery and medical robotics in the cranial area, Biomed Imaging Intery J 2007; 3(1):e11.

DETAILED DESCRIPTION OF EMBODIMENTS

Figure 1:
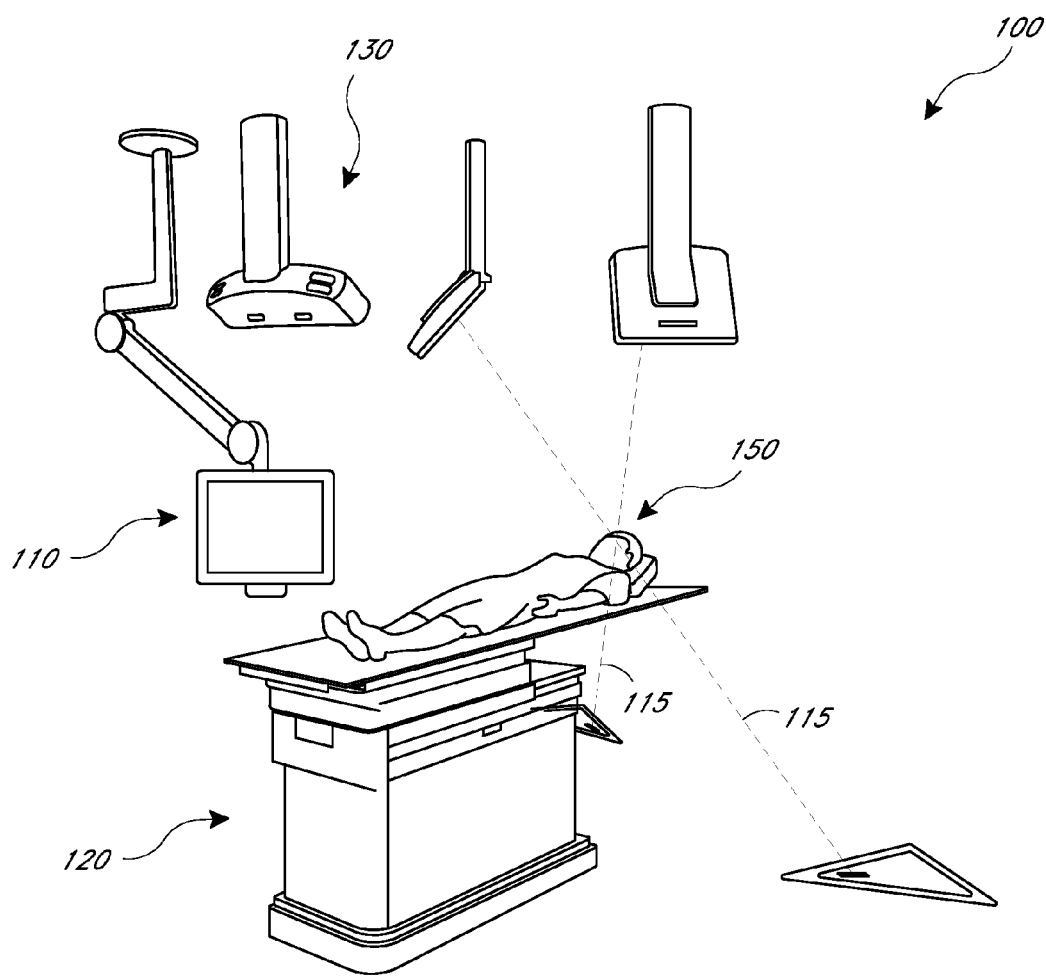
FIG. 1 illustrates a perspective view of an image-guided system and 6D robotic table according to one embodiment of the present application.

The present application provides for improved biopsy retrieval, drug delivery, and other treatments. According to one embodiment of the present application, a frameless image-guided biopsy system utilizes stereoscopic imaging, a 6-Dimentional (6D) Robotic couch system along with infrared cameras, and laser guidance for treatment. The depth of the target at any point is preferably determined using an optical distance indicator (ODI) installed on an isocentric C-arm. The accuracy of needle placement to the target can preferably be achieved to within 1 mm. Some treatments may include a technique for frameless stereotactic radiosurgery, as described herein.

According to one aspect of the application a method of performing a frameless image-guided biopsy uses stereoscopic imaging, a six-dimensional robotic couch system along with infrared cameras, a laser guidance system, an optical distance indicator, and a needle control apparatus. The system is adapted to obtain a biopsy sample from a patient with a high degree of accuracy and minimizing adverse patient effects comprises positioning a patient on a movable robotic couch in preparation for the collection of a biopsy sample. A planning CT scan is made of the patient with stereotactic fiduciary markers to produce digitally reconstructed radiographs. At least two stereoscopic images are generated using an imaging device to visualize and identify a target tumor. The at least two stereoscopic images identifying the target tumor are fused with the digitally reconstructed radiographs of the planning CT scan. Tumor location data is processed with a computer using the fused images. Movement instructions are communicated to the movable robotic couch in response to the tumor location data. The movable robotic couch shifts to position the target tumor of the patient at a known isocenter location. A biopsy needle is safely guided with a laser alignment mechanism towards the isocenter. The depth at which a needle is to be inserted to get to the target tumor is determined. The position and movement of the needle are controlled with a needle positioning apparatus. The needle is moved into the patient to the desired target tumor location. A biopsy sample of the target tumor is obtained.

Image Guided Systems

With reference to FIGS. 1-12, according to some embodiments, systems and features for image-guided biopsy or other treatments are provided. According to some embodiments, indications for image-guided biopsy may include, for example, confirming the primary tumor histo-pathology, metastasis in a patient with a known primary tumor, determining the nature of a solitary lesion, excluding malignancy in vertebral body compression, and investigating for infection. Among the various issues that may be considered are the site of lesion, the location of adjacent vital structures, the preferred approach, and the type and size of the needle. Systems and methods of treatment preferably comprise an advanced apparatus to do biopsy of various tumors in different organs of the body based on frameless stereotaxy and image guidance. The direction of the approach, as well as the depth at which the needle to be inserted are preferably guided by an isocentric laser system as discussed herein. The system is preferably equipped with an Optical Distance Indicator (ODI).

According to one aspect of the application, a surgical system and technique comprises taking one or more preoperative high resolution (Preferably 512×512 matrices) with 1 mm slice thickness MRI/PET/SPECT/US scans that best show the tumor. For some applications involving cranial and/or c-spine lesions, an immobilization mask that covers the mandible and the forehead is preferably provided for the patient. For some applications involving body and spine cases a Vac-Lok® system, or similar system, is preferably used to immobilize the patient. Three to five infrared fiduciary markers are preferably placed or positioned on the mask or the skin. In other embodiments more or less infrared fiduciary markers can be used.

A 1 mm slice thickness CT scan in high resolution (512× 512 matrix size or higher) with fiduciary markers is also taken. Then the images taken by the MRI/PET/SPECT/US scans are preferably fused with the CT scan. The target or targets are defined on the images. Image data, preferably including coordinates, the contour of the lesion and/or the organs at risk, along with a at least two DRRs are transferred to and/or communicated to a computer system 110, such as for example, the BrainLab ExacTrac Robotic computer or other suitable system.

With reference to FIG. 1, the patient is preferably positioned on the couch either supine or prone the same as the planning CT scan. The infrared fiduciary markers are placed on the patient. The patient is moved to the isocenter. Two stereoscopic images 115 of the target are taken. The stereoscopic images and the DRRs are fused, and the 6-D shifts are calculated. The shifts are transferred and/or communicated to a 6-D robotic couch top system 120. The infrared-based positioning and tracking system 130 cooperates and instructs the 6-D couch system 120 to move the target in the patient to the virtual isocenter of the couch and the laser system 140. The patient target is positioned so the target is at the virtual isocenter 150 of the couch 120 and laser system 140. Verification images are taken as outlined above and repeated until the target is within 0.5 mm or 0.5 degrees of the isocenter.

Depending on the approach, the laser system 140 focused on the target is positioned at the approach point determined by the surgeon. A needle support apparatus supporting the needle 160 is placed on the patient support system 120 and locked in place. The needle support system is aligned with the laser alignment system 140 of at least two planes to set the needle 160 angular direction using the coarse and fine micro-adjustment knobs. In some embodiments, the needle is preferably always aligned with three lasers, namely AP, lateral and axial focused at the isocenter.

Figure 2:
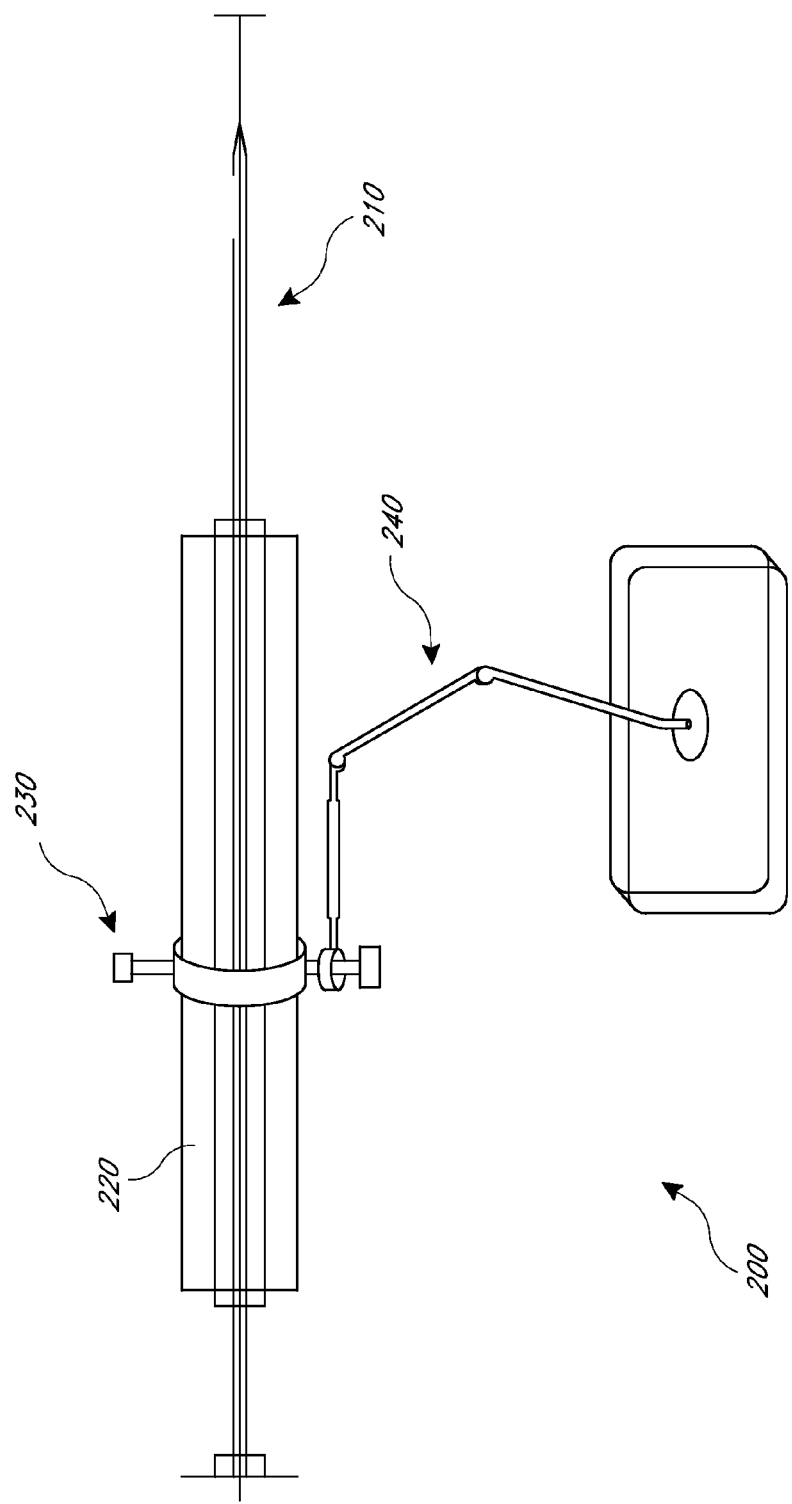
FIG. 2 illustrates a schematic view of a needle support and control system according to one embodiment of the present application.
Figure 3:
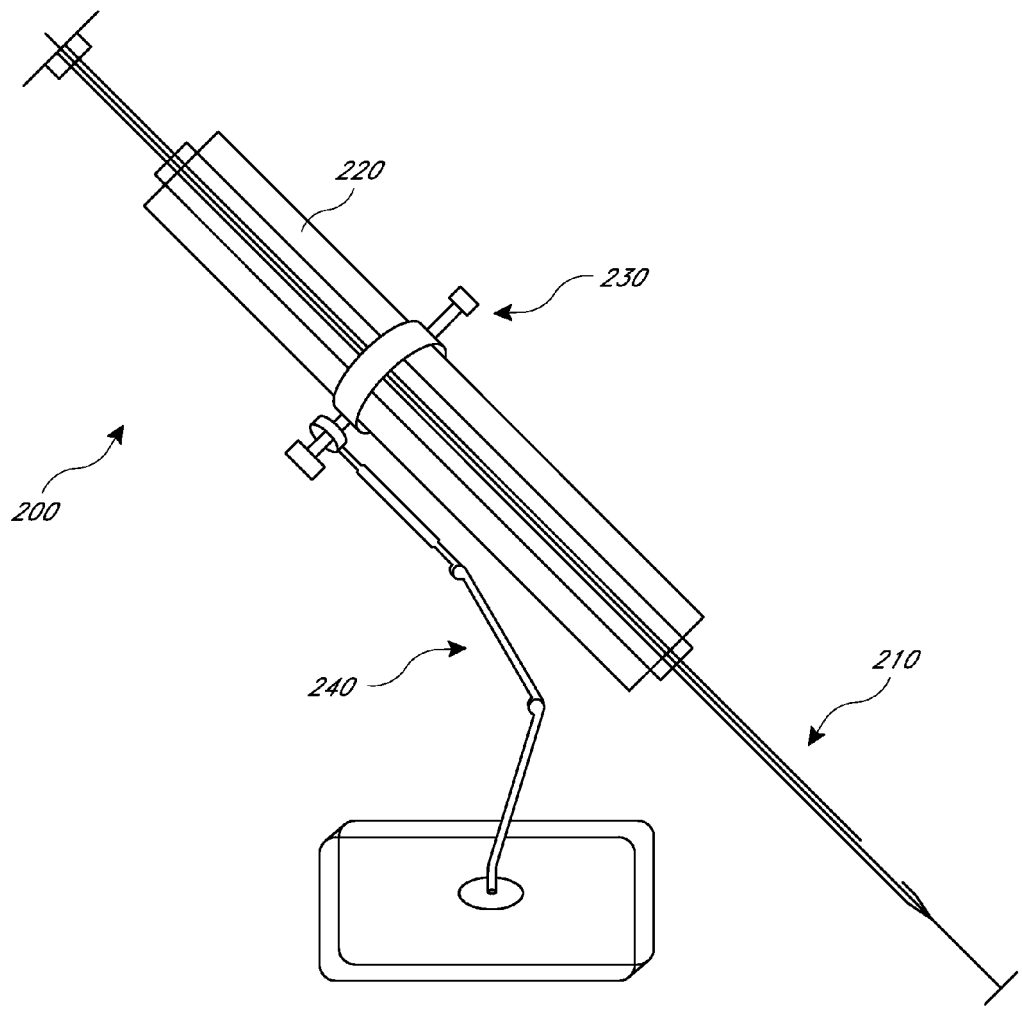
FIG. 3 illustrates a schematic view of the needle support and control system of FIG. 2 in another orientation.

FIGS. 2 and 3 show a laser guided injector system 200 according to one embodiment. The embodiment comprises laser lights, a syringe 210, a support plate 220, a screw 230 to hold the syringe in place, and a mechanism 240 to move the syringe in 6D (x, y, z, yaw, roll, and pitch). The syringe 210 is preferably installed on a support platform 220 and tightened with a holder's screw mechanism. Other fastening mechanisms are also possible. The entire support plate 220 is preferably attached to an articulating arm that can be adjusted in 6D and aligned with 2 laser systems in two different planes. The arm can be attached to the couch 120 supporting the patient. FIG. 2 shows the syringe in normal Cartesian coordinates, while FIG. 3 shows the syringe rotated by 45 degrees around the horizontal line.

Figure 4:
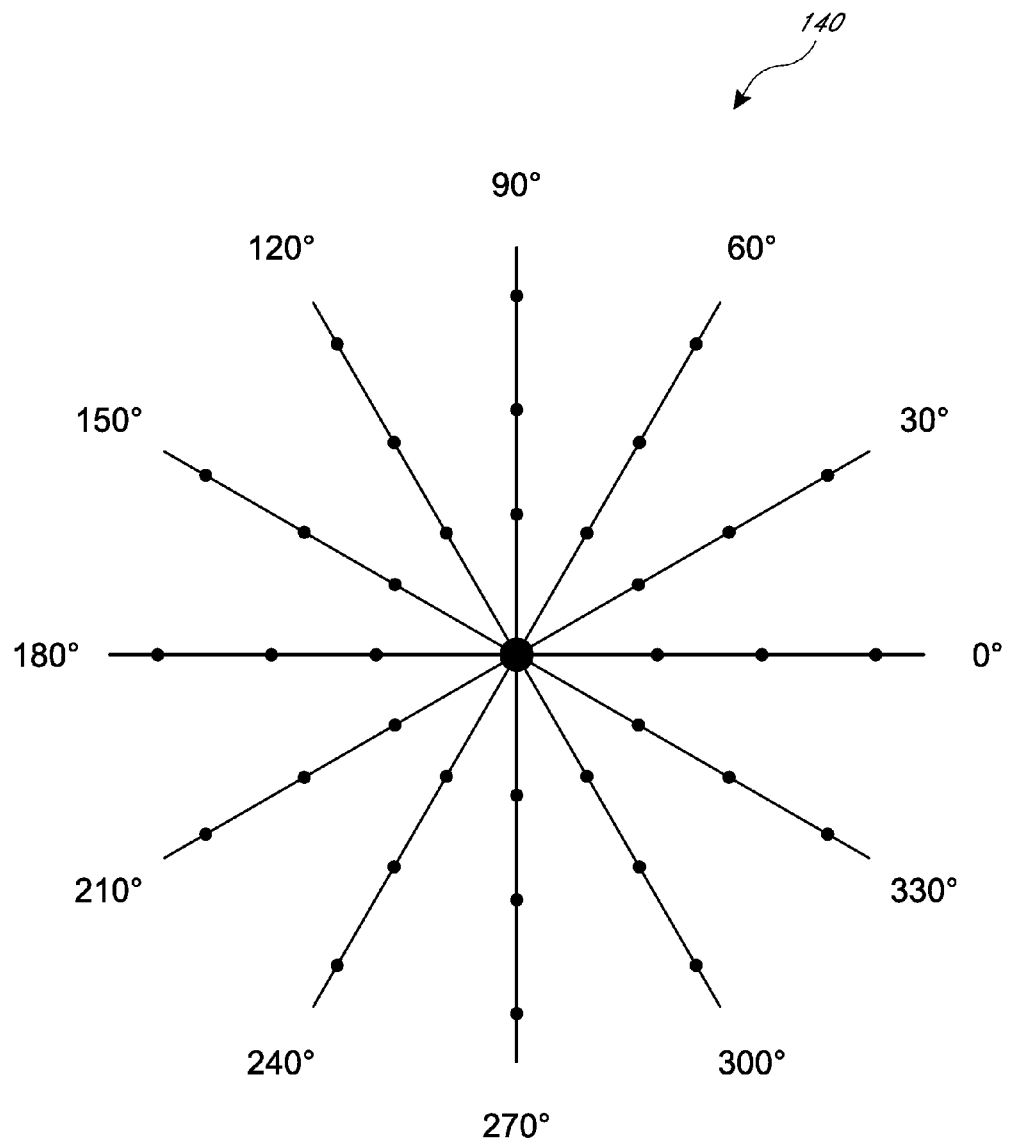
FIG. 4 illustrates a polar grid lens for use with a laser system according to one embodiment of the present application.
Figure 5:
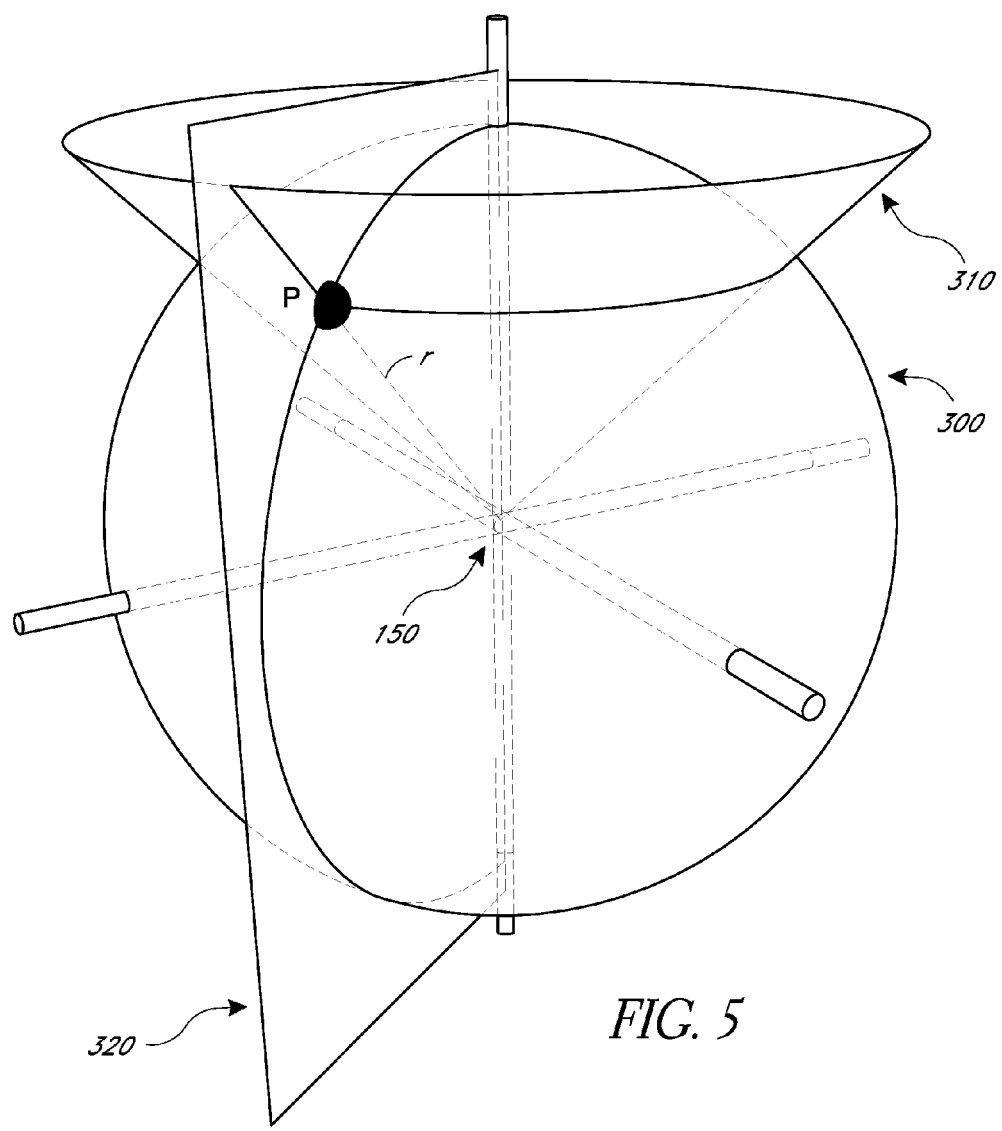
FIG. 5 illustrates a spherical coordinate system representative of locating an isocenter using a laser system according to one embodiment of the present application.
Figure 6:
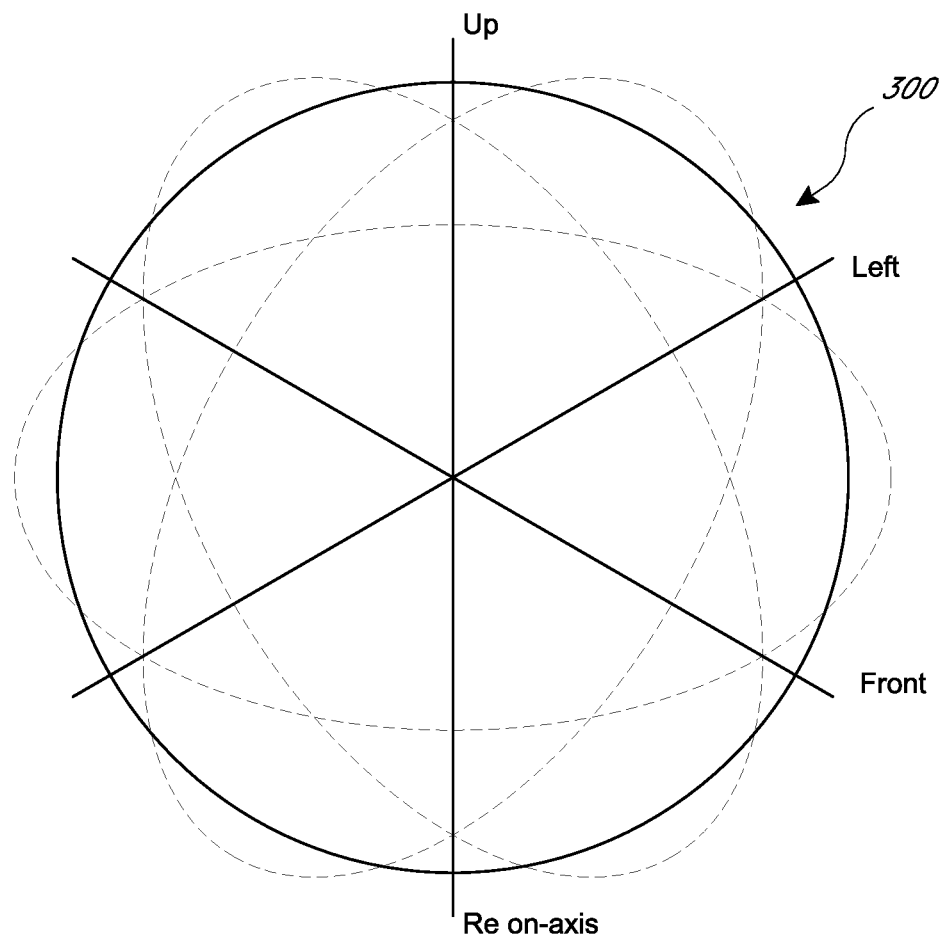
FIG. 6 illustrates another representation of the spherical coordinate system using a laser system according to one embodiment of the present application.

With reference to FIG. 4, a laser system 140 with a polar grid lens can be used to guide the needle 160 in several planes or angles. FIGS. 5 and 6 illustrate spherical coordinates. The center of the sphere 300 is preferably the target or virtual isocenter 150. There are many approaches to the isocenter 150. Approach points can be calculated by using the spherical coordinates. For example, sphere 300 shows the points where r=2. The cone 310 shows the points with inclination (or elevation) $\theta=45°$. The half-plane 320 shows the points with azimuth $\phi=-60°$. The zenith direction is vertical. The spherical coordinates (2, 45°, −60°) determine the point of space where those three surfaces intersect, shown as a point sphere representing the isocenter location.

The three coordinates (r, $\theta$, $\phi$) of a point P are defined as: the radial distance r is the Euclidean distance from the origin to the point P, the inclination $\theta$ is the angle between the zenith direction and the line formed between the origin and P, the azimuth $\phi$ is the angle between the reference direction on the chosen plane and the line from the origin to the projection of P on the plane. If the inclination $\theta$ is zero or 180°, the azimuth $\phi$ is indeterminate. If the radius r is zero, $\theta$ and $\phi$ are both indeterminate. The elevation angle is 90° minus the inclination angle. To plot a point from its spherical coordinates, go r units from the origin along the positive z-axis, rotate $\theta$ about the y-axis in the direction of the positive x-axis and rotate $\phi$ about the z-axis in the direction of the positive y-axis.

Figure 7:
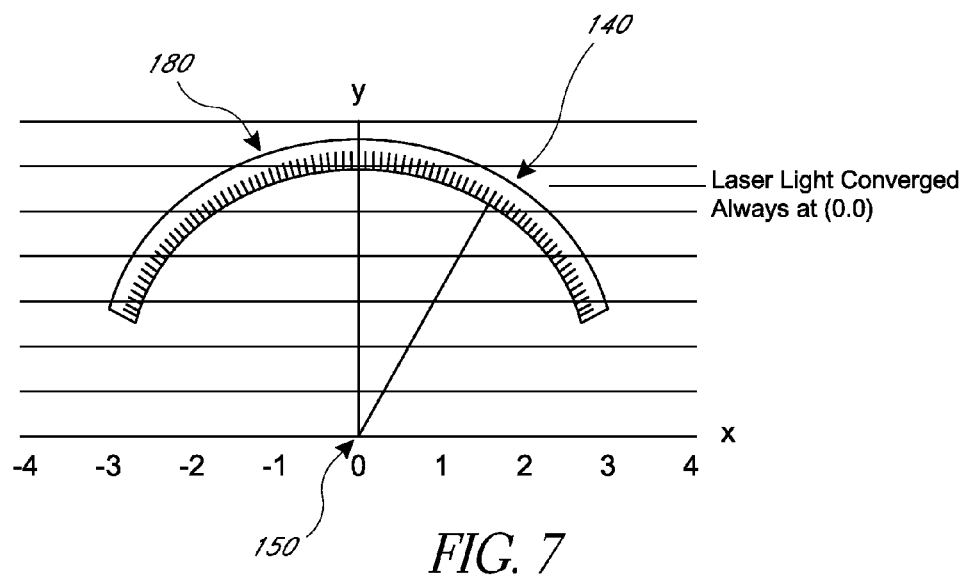
FIG. 7 illustrates a view of a laser system and ODI assembly according to one embodiment of the present application in use with a C-arm ceiling installation.
Figure 8:
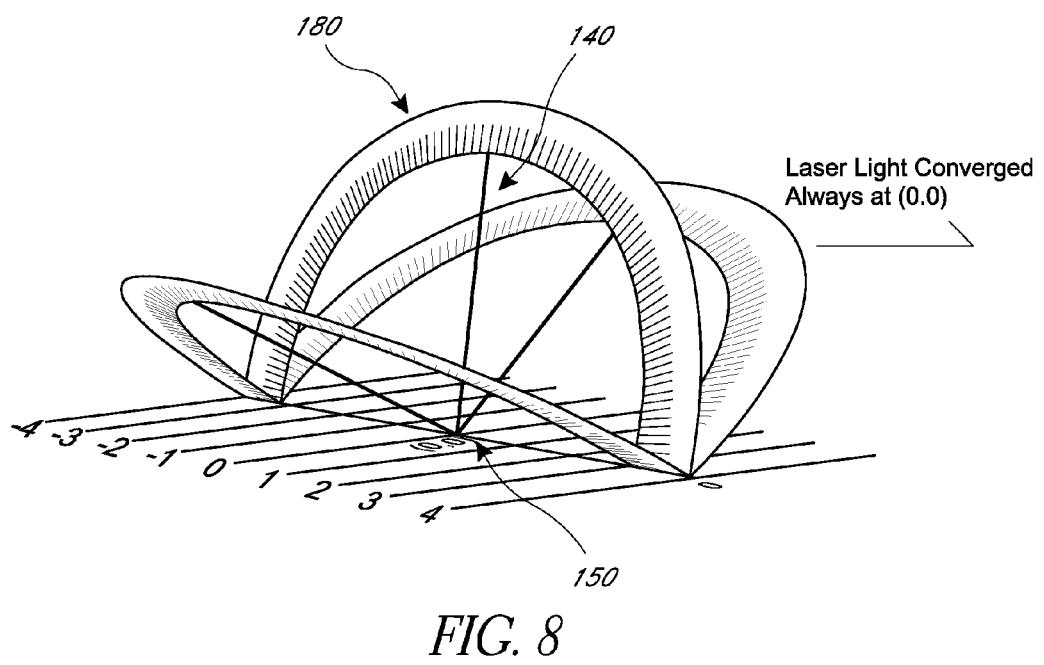
FIG. 8 illustrates a view of a laser system and ODI assembly on a C-arm according to one embodiment of the present application.
Figure 9:
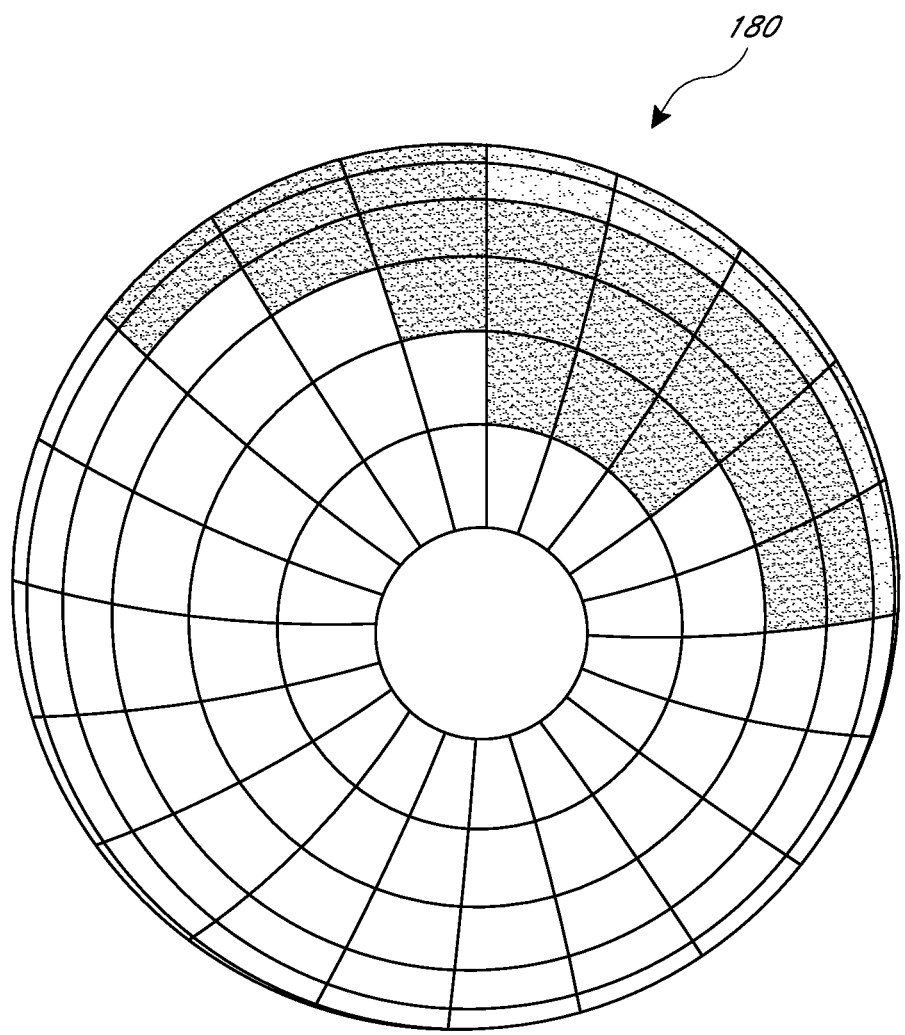
FIG. 9 illustrates a view of a sphere representing the pivotability and configurations of the C-arm according to one embodiment of the present application.

FIG. 7 shows a laser emitting a cross hair (+) converging at the isocenter 150 that can move with a motorized driver on the C-arm 180 installed from the ceiling. FIG. 7 shows one embodiment of a laser light and ODI assembly on a C-Arm 180 that can travel from 270 to 90 degrees in X-Y coordinate of the room always focused at the isocenter. FIG. 8 shows the C-Arm 180 can pivot in Y-Z coordinate direction as well. With reference to FIG. 9, the C-Arm 180 can pivot in Y-Z coordinate direction as visualized in this sphere as the laser C-arm can be rotated every 10 degrees or continuously where the arcs are positioned.

The ODI on the laser system preferably shows the depth the needle has to be inserted. A marker stopper may be placed on the needle at that depth. The approach point preferably is marked, prepared, and cleaned with a sterilizing solution. The patient is locally anesthetized. For cranial lesions, a burr hole of about 3 mm is made. For other parts of the body, the skin is marked and locally anesthetized. The needle is inserted till the stop marker has reached to the skin. In some embodiments the needle insertion is controlled automatically by a computer system. The tissue sample is removed by the needle as a biopsy sample. The laser-ODI assembly will be described in more detail below.

In some embodiments, similar steps are performed for cytotoxic drug delivery into tumors. For example, instead of the needle biopsy, an infusion needle is inserted to the desired depth as described above and the drug is injected.

Laser-ODI System

In one embodiment, the laser-ODI assembly described above preferably has the following characteristics. A horizontal and vertical diode laser is assembled on a circular arm such as a C-arm. The laser emitting a cross hair (+) that preferably always converges at the isocenter can move from 270 to 90 degrees with a motorized drive on the C-arm installed from the ceiling in X-Y Coordinate. The entire C-Arm can pivot from 0 degrees to 150 degrees in Y-Z coordinate. The angle 0, and 0 shines the laser crosshair (+) from the ceiling on the couch top in X-Y direction.

In some embodiments, the lasers are preferably always converging at a virtual point in space at a predetermined fixed distance from about 100 to about 200 cm away from the surface of the laser system. Other fixed distances, greater than about 200 or less than about 100 can also be used. The laser and ODI assembly can move on a virtual spherical surface with radii of about 100 cm to about 200 cm. This preferably facilitates the procedure by making generally any biopsy approach point feasible. In one embodiment, the ODI preferably shows a value of 0 at the isocenter, and 100 cm where the light is mounted. Therefore, if a tumor is at the depth of 8 cm from skin, the ODI displays 8 on the skin, which is 92 cm to the ODI, light.

Figures 10A, 10B:
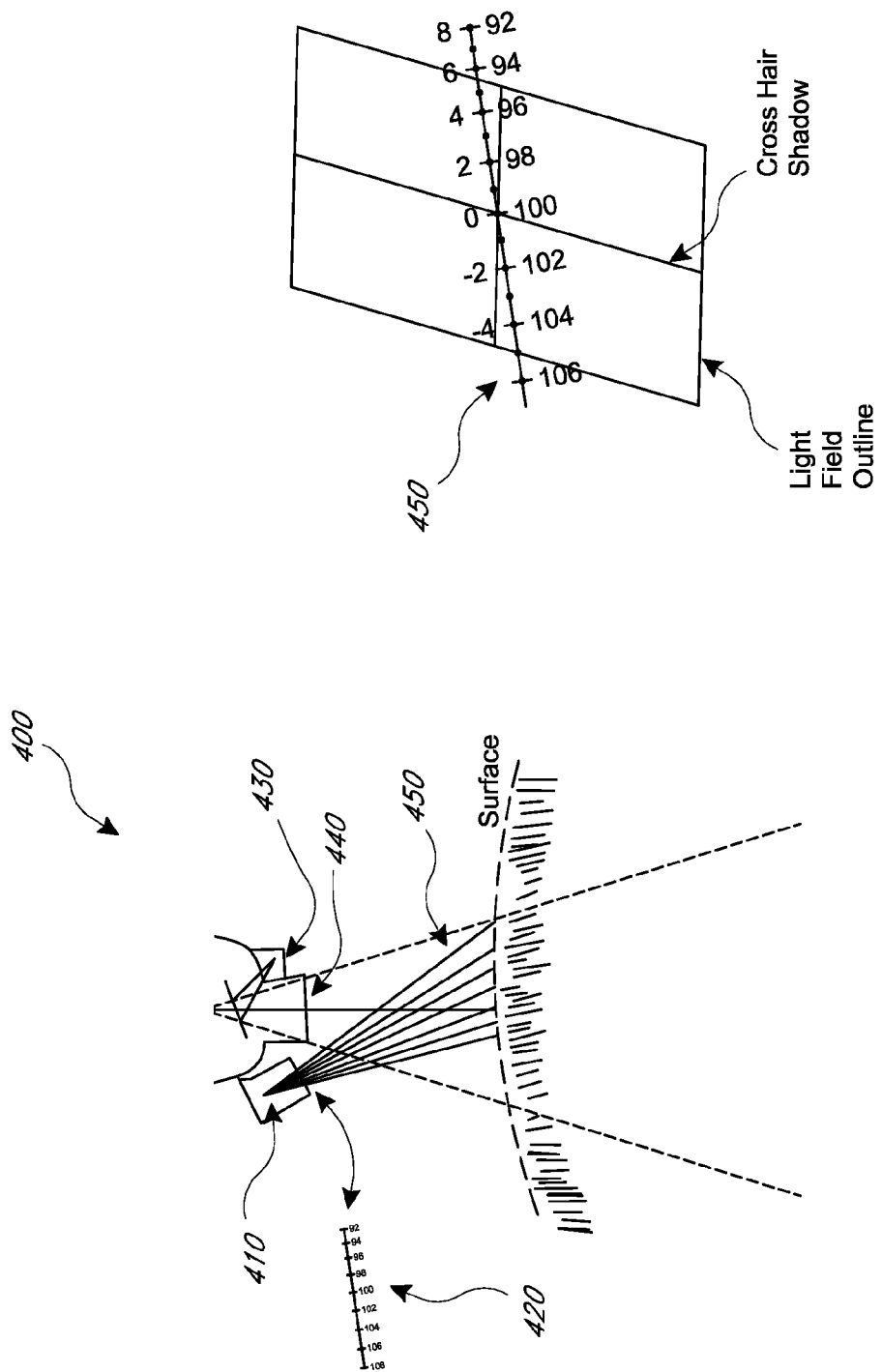
FIGS. 10A and 10B illustrate schematic views of the optical distance indicator according to one embodiment of the present application.

FIGS. 10a and 10b illustrate one embodiment of an Optical Distance Indicator system (ODI) 400. The ODI system 400 includes a distance indicator light 410, a graduated scale 420 mounted on the distance indicator, a field light 430, and cross hairs 440. According to one embodiment, the principles of operation of the optical distance indicator are as follows. With reference to FIG. 10a, the optical projection of a graduated ruler is shown at an angle with respect to the central ray of the beam. With reference to FIG. 10b, the projected scale is seen on the patient's body surface within the light beam.

As shown in FIG. 10a, the distance indicator comprises a light bulb coupled to an optical device that projects the gradations of an opaque scale at an angle with respect to the central axis of the beam. The rays of the fan beam emerging from the device meet the central axis of the radiation beam at different distances from the source. The gradations indicate the distance at which the different rays meet the central ray of the fan beam. The scale 450 as projected on the patient surface can be seen together with the light beam from the field localizer, as shown in FIG. 10b. The reading at the central ray of the beam (which is indicated by a cross-hair shadow in the light beam) is the source-to-surface distance, which is 100 cm in the figure.

In some systems, an alternative to the C-arm disclosed herein is a laser alignment system with a lens and micro adjustment assembly that generates a star pattern with up to 18-leg pairs, 10 degrees apart all passing through and converging at a single point at the isocenter 100 cm away from the laser face. The lens is preferably capable of generating an 18-line star pattern focused precisely at the isocenter 100 cm away from the laser source. In other embodiments, a different number of lasers could produce another pattern. According to one embodiment, the laser generates 18×18 possible points on the patient that could be used as the approach for the needle biopsy. Other similar laser assemblies on the other walls can guide the direction of the entry. For example, with 18 lines from the ceiling laser and similar wall systems, one has 18×18×18 points as options to approach the target for the biopsy.

An auto-navigation software and computer system is preferably provided to automatically calculate the best approach angle and entry point. This preferably is accomplished by contouring all the critical structures on a normal MR brain, including, for example, Angiography and Diffused Tensor Imaging of the brain, to identify and generate a data bank Atlas of the critical structures. The software then preferably automatically picks the entry point, and the angles based on factors such as the shortest traveling distance through the brain and selecting paths that do not go through critical structures such as, for example, the main arteries, veins (such as the sagittal sinus), and/or the motor and sensory fibers. The entry point coordinate and angles are preferably communicated or otherwise transferred to the laser system as outlined above. The needle preferably should enter at a point closest to the target, in a minimally invasive fashion. The needle preferably should not enter or exit through sensitive organs such as major arteries, veins, and sensitive motor and sensory structures of the brain. Similar software preferably maps body structures for other organs and parts of the body. For example, a mapping profile can be generated for spinal procedures or other areas.

Figure 11:
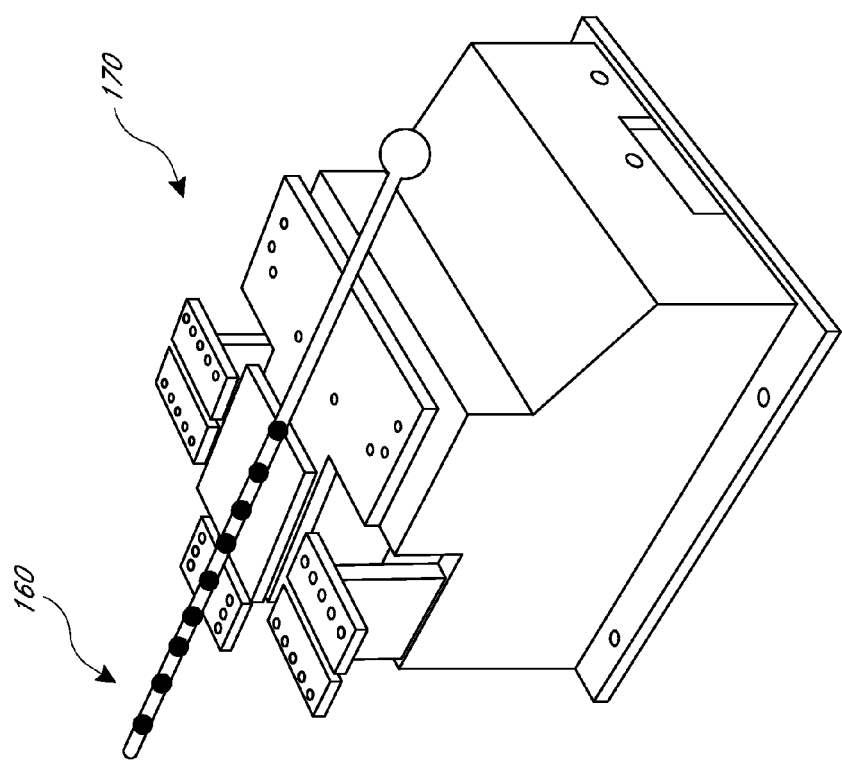
FIG. 11 illustrates a schematic view of a Hexapod® platform system for needle positioning according to one embodiment of the present application.

In some other embodiments, an alternative to laser guidance systems is installing the needle 160, for example, on a Hexapod® platform 170 with 6-Axis movements. FIG. 11 shows one embodiment comprising a high precision 6-Axis Hexapod® Platform System 170 manufactured by Physik Instrumente Corp. The Needle can be placed on the platform and guided by the Hexapod based on the Virtual Isocenter Coordinate System. The Coordinate of the tip of the needle on the Hexapod can be calibrated geometrically in 6D and Set to Zero at the isocenter 150. The isocenter coordinate can be automatically transferred from the ExacTrac computer to the Hexapod controller in some embodiments. The coordinates of the target placed at the isocenter are transferred to the Hexapod. The Hexapod automatically positions the tip of the needle at the isocenter. The Hexapod preferably has 5 infrared markers that locate its position. Other embodiments can have more or fewer markers. The tip of the needle position preferably can be identified by the dual infrared cameras at all times. The needle is advanced by the platform controls to reach to the isocenter. The biopsy needle is then inserted into the guide needle. Tissue samples are removed for examination. The Hexapod controller can be programmed for proper velocity, positioning and critical area coordinates to avoid accidental insertion through critical structures.

In some embodiments, an alternative system and method uses a needle holder with at least five fiduciary infrared markers. A different number of infrared markers is also possible. The tip of the needle is identified relative to the fiduciary markers. After the patient is positioned at the isocenter, a CT image of the needle holder is brought up in the ExacTrac computer system, or another suitable computer control system. The needle holder preferably works like a wand and can be positioned on the patient's skin to get to the approach point. The needle can be inserted to reach the isocenter. FIG. 1 shows one embodiment comprising a BrainLab ExacTrac Image Guided Radiosurgery System. This system can be adapted to accommodate for frameless tumor biopsy as well as treatment delivery directly into the tumors using cytotoxic chemotherapy or radioactive seeds into the lesions as discussed herein.

Figure 12:
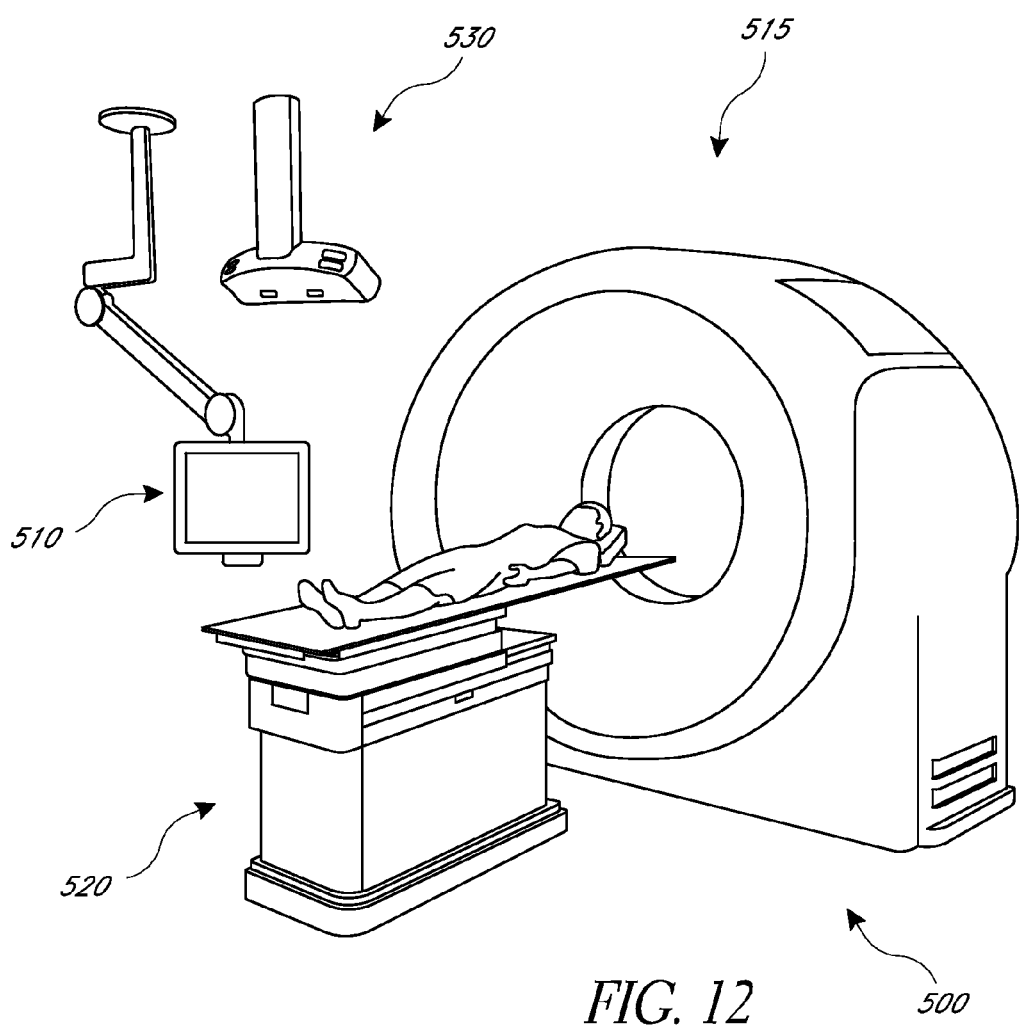
FIG. 12 illustrates a schematic view of a CT or MR image-guided surgery system according to one embodiment of the present application.

FIG. 12 shows an alternative embodiment 500 using similar techniques that can be applied using CT guided or MRI guided intervention 515 instead of stereoscopic imaging 115. This can be accomplished for example by scanning the patient, identifying the isocenter on the planning computer 510, moving the patient to the isocenter using the 3D or 6D couch system 520, and guiding the intervention instrument to the isocenter using the ODI, and laser alignment systems such as those described above. In some embodiments a motorized laser alignment system can be designed to automatically move the ceiling and the wall lasers to converge at the virtual isocenter instead of moving the couch system. The 3-dimensional CT or MRI guided localization 515 described herein may yield a more accurate localization of soft tissue targets not close to bony landmarks.

It will be apparent to those skilled in the art that various modifications and variations can be made in the present embodiments and methods without departing from the scope or spirit of the advantages of the present application. Thus, it is intended that the present application cover the modifications and variations of these embodiments and their equivalents.

What is claimed is:

1. A system for frameless image-guided biopsy using stereoscopic imaging, the system comprising:
   a first preoperative imaging system for capturing a planning CT scan of a patient with stereotactic fiduciary markers to produce digitally reconstructed radiographs of the patient;
   a second preoperative imaging system for capturing a preoperative high resolution scan of the patient to produce target images of a tumor of the patient;
   a planning computer system in communication with the first and second preoperative imaging systems to fuse the digitally reconstructed radiographs of the planning CT scan with the target images of the preoperative high resolution scan to provide image data comprising target information;
   an operating room computer system in communication with the planning computer system to receive the image data and target information;
   an operating room imaging system in communication with the operating room computer system, the operating room imaging system for capturing a plurality of stereoscopic images of the patient to send to the operating room computer system wherein the plurality of stereoscopic images are fused with the image data to provide tumor location data;
   a six-dimensional robotic couch system configured to support the patient during use and in communication with the operating room computer system to receive tumor location data and shift position in response to infrared position data received to position the tumor of the patient at an isocenter location;
   a laser guidance system comprising a laser alignment mechanism mounted at least partially above the six-dimensional robotic couch system and in communication with the operating room computer system directing a plurality of alignment lasers toward the isocenter location;
   an optical distance indicator in communication with the operating room computer system, for optically sensing the position of the patient through the use of radiographic markers and infrared technology, and for indicating a depth of the target tumor location within the patient; and
   a needle positioning apparatus comprising a needle support and a needle, the needle support coupled to the six-dimensional robotic couch system and adapted to align the needle with a laser generated by the laser guidance system and directed toward the isocenter at a desired entry location, wherein the needle is adapted to be advanced to the depth of the target tumor location provided by the optical distance indicator to obtain a biopsy sample from the patient for analysis.

2. The system of claim 1, wherein the second preoperative imaging system comprises one or more of an MRI, PET, SPECT, and ultrasound imaging device.

3. The system of claim 1, wherein the robotic couch system comprises a robotic table adapted to shift in six dimensions.

4. The system of claim 1, wherein the needle positioning apparatus has an articulating arm.

5. The system of claim 1, wherein the needle positioning apparatus is in communication with the operating room computer system and wherein movement of the needle is automatically controlled using the operating room computer system.

6. A system for frameless image-guided intervention using stereoscopic imaging, the system comprising:
 a first preoperative imaging system for capturing a planning CT scan of a patient with stereotactic fiduciary markers to produce digitally reconstructed radiographs of the patient;
 a second preoperative imaging system for capturing a preoperative high resolution scan of the patient to produce target images of a location within the patient;
 a planning computer system in communication with the first and second preoperative imaging systems to fuse the digitally reconstructed radiographs of the planning CT scan with the target images of the preoperative high resolution scan to provide image data comprising target information;
 an operating room computer system in communication with the planning computer system to receive the image data and target information;
 an operating room imaging system in communication with the operating room computer system, the operating room imaging system for capturing a plurality of stereoscopic images of the patient to send to the operating room computer system wherein the plurality of stereoscopic images are fused with the image data to provide target location data;
 a robotic couch system configured to support the patient during use and in communication with the operating room computer system to receive target location data and shift position in response to data received to position the target at an isocenter location;
 a laser guidance system comprising a laser alignment mechanism in communication with the operating room computer system directing at least one alignment laser toward the isocenter location;
 an optical distance indicator in communication with the operating room computer system, for optically sensing the position of the patient through the use of radiographic markers and infrared technology, and for indicating a depth of the target location within the patient; and
 a needle positioning apparatus comprising a needle support and a needle, the needle support coupled to the robotic couch system and adapted to align the needle with the at least one alignment laser generated by the laser guidance system and directed toward the isocenter at a desired entry location, wherein the needle is adapted to be advanced to the depth of the target location provided by the optical distance indicator in a patient intervention.

7. The system of claim 6, comprising an immobilizing mask system adapted to cover at least a portion of a face of the patient.

8. The system of claim 7, wherein the second preoperative imaging system comprises an MRI imaging device.

9. The system of claim 7, wherein the second preoperative imaging system comprises a PET imaging device.

10. The system of claim 7, wherein the second preoperative imaging system comprises a SPECT imaging device.

11. The system of claim 7, wherein the second preoperative imaging system comprises an ultrasound imaging device.

12. The system of claim 7, wherein the needle positioning apparatus is in communication with the operating room computer system and wherein movement of the needle is automatically controlled using the operating room computer system.

13. A system for frameless image-guided intervention using stereotactic space, the system comprising:
 a first preoperative imaging system for capturing a planning CT scan of a patient with stereotactic fiduciary markers to produce digitally reconstructed radiographs of the patient;
 a second preoperative imaging system for capturing a preoperative high resolution scan of the patient to produce target images of a location within the patient;
 a planning computer system in communication with the first and second preoperative imaging systems to fuse the digitally reconstructed radiographs of the planning CT scan with the target images of the preoperative high resolution scan to provide image data comprising target information;
 an operating room computer system in communication with the planning computer system to receive the image data and target information;
 an operating room imaging system in communication with the operating room computer system, the operating room imaging system for capturing a plurality of images of the patient to send to the operating room computer system wherein the plurality of images are fused with the image data to provide target location data;
 a robotic couch system configured to support the patient during use and in communication with the operating room computer system to receive target location data and shift position in response to data received to position the target at an isocenter location;
 a laser guidance system comprising a laser alignment mechanism in communication with the operating room computer system directing at least one alignment laser toward the isocenter location;
 an optical distance indicator in communication with the operating room computer system, for optically sensing the position of the patient through the use of radiographic markers and infrared technology, and for indicating a depth of the target location within the patient; and
 an intervention instrument coupled to the robotic couch system and adapted to be aligned with the at least one alignment laser generated by the laser guidance system and directed toward the isocenter at a desired entry location, wherein the intervention instrument is adapted to be advanced to the depth of the target location provided by the optical distance indicator in a patient intervention wherein the intervention instrument is a needle.

14. The system of claim 13, wherein the second preoperative imaging system comprises one or more of an MRI, PET, SPECT, and ultrasound imaging device.

15. The system of claim 14, wherein the operating room imaging system comprises a stereoscopic imaging device.

16. The system of claim 14, wherein the operating room imaging system comprises a CT imaging device.

17. The system of claim 14, wherein the operating room imaging system comprises an MRI imaging device.

18. The system of claim 14, wherein the intervention instrument is in communication with the operating room computer system and wherein movement of the intervention instrument is automatically controlled using the operating room computer system.

19. The system of claim 18, wherein the intervention instrument comprises a biopsy needle.

20. The system of claim 18, wherein the intervention instrument comprises a syringe.

* * * * *